(12) United States Patent
Park

(10) Patent No.: US 9,655,723 B2
(45) Date of Patent: May 23, 2017

(54) ONE-WAY HEART ASSIST VALVE

(71) Applicant: Bret J. Park, South Jordan, UT (US)

(72) Inventor: Bret J. Park, South Jordan, UT (US)

(73) Assignee: Savant Holdings LLC, South Jordan, UT (US)

( * ) Notice: Subject to any disclaimer, the term of this patent is extended or adjusted under 35 U.S.C. 154(b) by 79 days.

(21) Appl. No.: 13/959,047

(22) Filed: Aug. 5, 2013

(65) Prior Publication Data

US 2015/0039076 A1    Feb. 5, 2015

(51) Int. Cl.
- A61F 2/24 (2006.01)
- A61M 1/12 (2006.01)
- A61M 1/10 (2006.01)
- A61F 2/82 (2013.01)

(52) U.S. Cl.
CPC ......... *A61F 2/2475* (2013.01); *A61M 1/1096* (2014.02); *A61M 1/122* (2014.02); *A61F 2/82* (2013.01)

(58) Field of Classification Search
CPC .................................................. A61M 5/00
USPC ............ 623/1.11–1.54, 2.1–2.22, 2.26–2.34; 604/246–249
See application file for complete search history.

(56) References Cited

U.S. PATENT DOCUMENTS

| | | | |
|---|---|---|---|
| 5,827,237 A * | 10/1998 | Macoviak | A61M 25/0075 604/246 |
| 6,299,637 B1 | 10/2001 | Shaolian et al. | |
| 6,719,787 B2 | 4/2004 | Cox | |
| 6,736,846 B2 | 5/2004 | Cox | |
| 6,945,957 B2 | 9/2005 | Freyman | |
| 7,503,928 B2 | 3/2009 | Case et al. | |
| 7,530,995 B2 * | 5/2009 | Quijano et al. | 623/1.24 |
| 7,637,937 B2 | 12/2009 | Case et al. | |
| 7,776,053 B2 | 8/2010 | Strecker | |
| 7,867,274 B2 | 1/2011 | Hill et al. | |
| 8,012,198 B2 | 9/2011 | Hill et al. | |
| 8,128,681 B2 | 3/2012 | Chouinard et al. | |
| 8,246,676 B2 | 8/2012 | Acosta et al. | |
| 8,303,649 B2 | 11/2012 | Agnew et al. | |
| 8,377,115 B2 | 2/2013 | Thompson | |

(Continued)

FOREIGN PATENT DOCUMENTS

| | | |
|---|---|---|
| CA | 2407062 | 10/2001 |
| EP | 0 937 439 B1 | 9/2003 |

(Continued)

*Primary Examiner* — Yashita Sharma
(74) *Attorney, Agent, or Firm* — Austin Rapp & Hardman

(57) ABSTRACT

A medical device used in patients with inefficient heart function to improve the efficiency of the pumping action of the heart. This device adds one or more one-way valves in the blood vessels and/or arteries, very near, but not in, the heart, thereby increasing the efficiency of the native heart. The device includes one or more one-way heart valves designed to go in arteries/veins that are connected to the heart, and which arteries and/or veins are the conduits for taking blood into/out of the heart. The one-way heart valve allows blood flow in only one direction. An optional sleeve (stent) may be placed outside the arteries/veins where the valve(s) are located to add support to the walls. An optional sleeve (stent) may also be used on the inside of the artery to insure the artery does not collapse during a vacuum phase of the beating.

11 Claims, 4 Drawing Sheets

(56) References Cited

U.S. PATENT DOCUMENTS

| | | |
|---|---|---|
| 8,470,022 B2 | 6/2013 | Johnson |
| 8,470,023 B2 | 6/2013 | Eidenschink et al. |
| 8,540,768 B2 | 9/2013 | Stacchino et al. |
| 8,556,960 B2 | 10/2013 | Agnew et al. |
| 8,579,966 B2 | 11/2013 | Seguin et al. |
| 8,870,944 B2 * | 10/2014 | Sochman et al. ............ 623/1.24 |
| 2002/0062146 A1 * | 5/2002 | Makower ......... A61B 17/00234 623/1.13 |
| 2009/0024152 A1 * | 1/2009 | Boyden ................. G06Q 50/22 606/155 |
| 2010/0298927 A1 * | 11/2010 | Greenberg ............ A61F 2/2418 623/1.26 |
| 2011/0251678 A1 | 10/2011 | Eidenschink et al. |

FOREIGN PATENT DOCUMENTS

| | | |
|---|---|---|
| WO | WO 01/76510 A3 | 10/2001 |
| WO | WO 2008/085895 A2 | 7/2008 |

* cited by examiner

ONE-WAY HEART ASSIST VALVE

TECHNICAL FIELD

The present embodiments relate to a heart/artery/vein valve device. More particularly, the present embodiments relate to a heart/artery/vein valve device designed to help patients with congestive heart failure or leaking heart valves.

BACKGROUND

Approximately 23 million people worldwide are afflicted with congestive heart failure ("CHF") and two (2) million new cases of CHF are diagnosed each year worldwide. In contrast to other cardiovascular disorders that have actually declined during the past few decades, the incidence of CHF is currently on the rise. In fact, CHF is one of the most rapidly growing cardiovascular disorders in the United States.

CHF is a chronic inability of the heart to either: a) maintain an adequate output of blood from one or both ventricles of the heart to meet the metabolic demands of the tissues, or; b) adequately circulate blood in one direction through the body, without backflow, (also known as regurgitation).

In a case of CHF, the left ventricle, the right ventricle or both the left and right ventricles generally are weakened such that the volume of blood the heart is able to move may be insufficient for the patient's body. Similarly, if the valves of the heart are leaking (i.e., allowing some blood to regurgitate or flow backwards), fluid may build up behind the heart. With a weakened left ventricle or right ventricle or both, significant problems may occur.

For example, with a weakened left ventricle or right ventricle or both, there is a shift of large volumes of blood from the systemic circulation flow into the pulmonary (lung) circulation flow. If the inability to move the volume of blood forward is due to a left heart side problem (without the right side failing as well), blood continues to be pumped into the lungs by the normal right heart side, while the blood is not pumped adequately out of the lungs by the left heart side. As the volume of blood in the lungs increases, the pulmonary vessels enlarge, pulmonary venous congestion develops, and, once the pulmonary capillary pressure rises above a critical point, fluid begins to filter out of the capillaries into the lung's interstitial spaces and alveoli (air sacs in the lungs where exchange of oxygen and carbon dioxide occurs). Such conditions generally result in pulmonary edema and may subsequently lead to pleural effusion and abdominal effusion.

If the abnormality lies in the right heart side or the pulmonary arteries, this condition limits the ability to move blood forward (i.e., limits the flow of blood to the rest of the body). During this condition, congestion occurs behind the right heart side (causing pleural effusion and/or build-up of fluid in the abdomen). If the left side heart valve allows fluid to regurgitate (flow backwards, upon contraction of the heart), this condition may cause the kidneys and liver to fail, due to fluid build-up therein, and excessive pressure as fluid pressurizes in those organs instead of simply flowing through them. Ultimately, if the patient has a weakened left ventricle or right ventricle or both, the patient will, over time, require a heart transplant and/or will die.

CHF is often caused by a lower non-functioning valve within the heart. CHF also causes valves that may be working properly to stop working properly as the heart increases in size to compensate for its lack of efficiency. As the heart becomes inefficient, the body compensates by increasing the size of the heart which often causes the heart valves to leak. Moreover, as the heart increases in size, the heart grows into the pericardium (which is the sac covering the heart). This condition may cause the pericardium to inflame. At the same time, when the heart expands, it begins to work excessively hard and cannot expand and contract as it needs to. Thus, the expanding heart further makes treatment of CHF difficult.

When treating CHF, drugs are typically given to the patient which cause the patient's heart to beat harder. Alternatively, the drugs cause a thickening or thinning of the blood. While these drugs may help individual patients, they generally do not provide a long-term solution for the patient's heart problems. Accordingly, a second treatment given to the patient may involve invasive surgery, wherein the chest is cut open and a new valve (either artificial or biological) is installed to replace the old (natural) valve, or the natural valve is repaired. A third solution involves a valve replacement similar to the second solution but does so less intrusively by going through smaller holes and performing the surgery endoscopically. The last, and most costly treatment of CHF is a full-blown heart transplant for the patient. Of course, heart transplants are prohibitively expensive and there is currently a shortage of heart donors. After a patient receives a heart transplant, drugs are required to suppress the immune system of the patient to prevent the patient's immune system from attacking the new heart. This presents an entirely new set of potential problems for the transplant patient, with respect to the patient's suppressed immune system.

Because all of the valve replacement solutions require the heart to be cut open, they are very damaging to the heart itself. This means that patients with an extremely weak heart oftentimes cannot survive this type of surgery, even if such a surgery would be otherwise beneficial. If a doctor deems a patient too weak to survive the surgery, the doctor will generally abstain from performing the valve surgery and put a patient on the "waiting list" to receive a heart transplant. Because of the lack of available transplant hearts, and the weakness of the patients awaiting these hearts, many patients die before they have a chance to receive a transplant. Although advances in pharmacology have led to better treatment, 50% of the patients with the most advanced stage of CHF generally die within one year.

U.S. Pat. Nos. 6,719,787 and 6,736,846 both teach heart surgery procedures and devices in which the native heart valve is removed and a new valve is added to the patient. Such procedures still require the patient's heart valves or other valves to be removed and thus involve difficult surgeries.

Heart valve surgery is very intrusive and therefore another solution is needed wherein the heart itself does not have to be cut open. The present embodiments provide this type of solution. More particularly, the present embodiments provide a mechanism whereby a patient who has CHF can have valves placed into veins and arteries that are near the heart but not in the heart itself, which will allow the heart itself to pump more efficiently. This solution may enable many patients with heart disease who would otherwise die or require a heart transplant to be able to have a normal functioning life with a much less intrusive surgery. Furthermore, the present embodiments may prevent a patient who otherwise would need a heart transplant, to never actually need a heart transplant. For these patients, the need for drugs (which may lower the patient's immune system and/or have less desirable other side-effects) may be obviated. Furthermore, because the present embodiments are less intrusive to the heart, it may also be beneficial and an alternative for patients who could not survive the prior art heart valve replacement/repair surgery. Additionally, the present embodiments may be provided endoscopically, and thus the surgery associated with the present embodiments can be minimal.

SUMMARY

The present embodiments relate to a heart/artery/vein valve device and a new way to use these devices to help people with congestive heart failure or leaking heart valves. This valve device is an alternative to conventional heart valve repair or valve replacement within the heart. This valve device may be used outside of the heart itself but will assist the heart to correctly displace the blood. In some embodiments, the valve device may involve placing one-way valves strategically in arteries and veins before and/or after the heart. This device may be a less intrusive means of solving congestive heart failure, and in some cases, may eliminate the need for the patient to undergo heart transplant surgery.

In some embodiments, a first set of one-way valves are placed in one or more veins upstream of the heart and a second set of one-way valves are placed in one or more arteries downstream of the heart. These valve(s) may work together to regulate the blood flow and prevent regurgitation or backflow of blood. In some embodiments, these valve(s) may be placed in the veins/arteries without removing the heart's naturally-occurring valves. Such embodiments may be beneficial because the patient may not have to have his/her heart cut open, as would otherwise be required to remove/replace one of the heart's valves.

Although some embodiments may involve the use of multiple valves (such as, for example, one or more valves in an artery and one or more valves in a vein), there will be other embodiments which may be constructed in which only a single valve is used. For example, this single valve could be placed in an artery. In other embodiments, this single valve could be placed in a vein. Obviously, the exact number of valves, along with the placement of the valves, will depend upon the patient's condition, etc.

DETAILED DESCRIPTION

The present embodiments relate to a new type of heart device that will help patients who have heart defects or suffer from CHF. While the present embodiments are designed for human patients, animals could also benefit from the present embodiments. In other words, in addition to doctors installing the present embodiments into human patients who have heart problems, veterinarians could install the present embodiments into animals that are likewise suffering from heart problems. Also, the present embodiments could be installed in humans that are just developing heart problems (e.g., who have never had "heart surgery" before) or to those patients who have previously undergone heart surgery and/or who have previously received a mechanical valve in their heart.

Figure 1A:
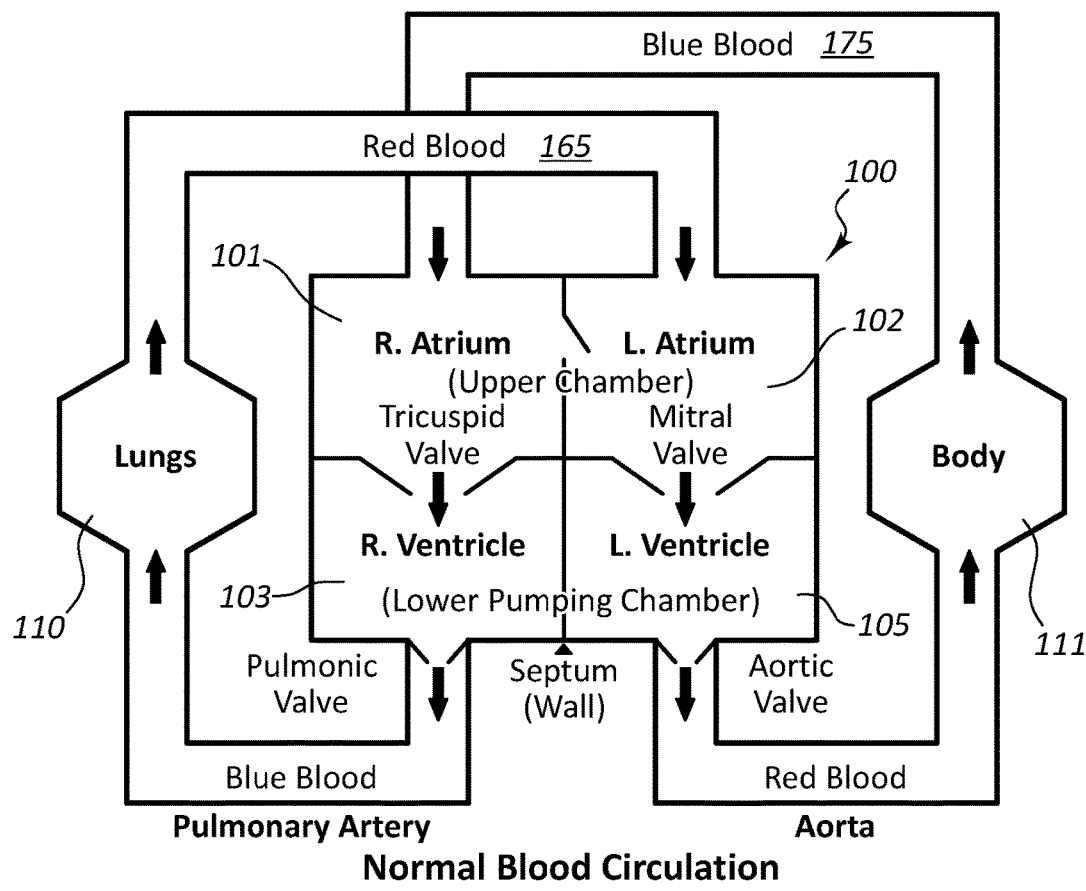
FIG. 1A is a schematic drawing of the blood flow into and out of the heart according to the prior art.

In order to understand the present embodiments, it is first necessary to understand the flow of blood into and out of the heart as well as the operation of valves within the heart. FIG. 1A represents a schematic drawing of blood flow into and exiting a human heart. Specifically, as shown in FIG. 1, the heart 100 includes four (4) chambers, namely the right atrium 101, the right ventricle 103, the left atrium 102 and the left ventricle 105. The arrows in FIG. 1A represent the direction of blood flow. The "red blood" 165, as shown by arrows in FIG. 1A, contains oxygen from the lungs 110 and enters the left atrium 102. This red blood 165 is carried from the lungs 110 to the heart 100 via four (4) pulmonary veins (i.e., there are two pulmonary veins for each lung 110). The heart 100 pumps the red blood 165 through the mitral valve (inside the heart) from the left atrium 102 into the left ventricle 105. The red blood 165 then leaves the left ventricle 105, through the aortic valve, into the aorta and is then taken via the body's artery system throughout the body 111. The veins of the body 111 will return "blue blood" 175 (i.e., blood lacking oxygen) to the right atrium 101 of the heart 100. (In general, the blue blood 175 flows through the veins of the body 111 to either the superior vena cava (which returns blood 175 from the upper portion of the body 111) or the inferior vena cava (which returns blood 175 from the lower portion of the body 111). The blue blood 175 will flow through both the inferior vena cava and the superior vena cava into the right atrium 101 of the heart 100.

Once the blue blood 175 is in the right atrium 101, it will pass through the tricuspid valve into the right ventricle 103. The heart 100 then pumps the blue blood 175 out of the right ventricle 103 through the pulmonic valve and towards the lungs 110. The conduits that carry the blue blood 175 to the lungs 110 are referred to as the left and right pulmonary arteries. Once the blue blood 175 reaches the lungs 110, it is filled with oxygen (i.e., converted to red blood 165) and is returned to the left atrium 102 via the four pulmonary veins.

Figure 1B:
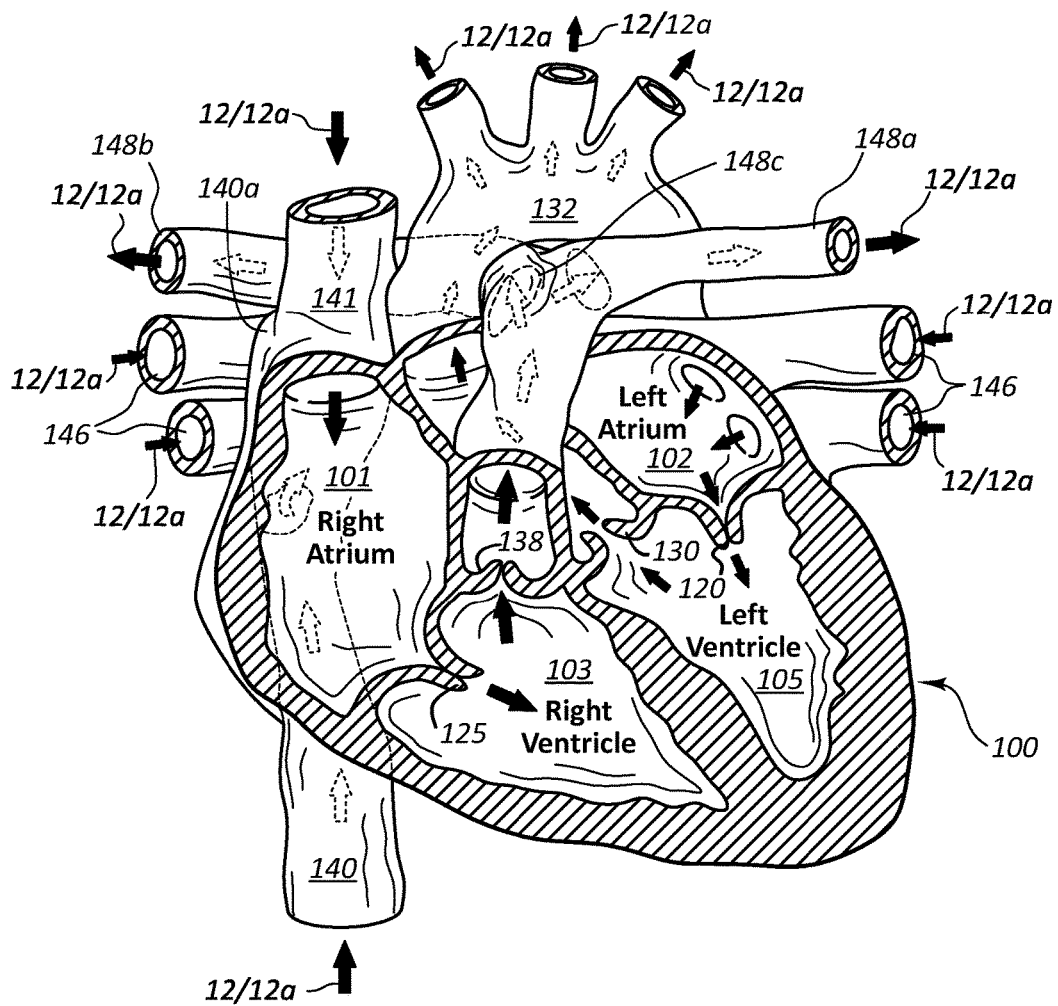
FIG. 1B is an isometric drawing of the heart and the veins/arteries that carry blood to and from the heart according to the prior art.

FIG. 1B shows a schematic drawing of the heart 100 and the various veins/arteries of FIG. 1A. In FIG. 1B, the direction of blood flow is represented by arrows labeled with reference numeral 12, while the blood itself is represented by reference numeral 12a. As shown in FIG. 1B, the heart 100 includes a mitral valve 120 that separates the left atrium 102 from the left ventricle 105. The tricuspid valve 125 separates the right atrium 101 from the right ventricle 103. Likewise, blood passes through the aortic valve 130 when it exits the heart 100 and enters the aorta 132.

There is no valve between the inferior vena cava 140 and the right atrium 101. Likewise, there is also no valve between the superior vena cava 141 and the right atrium 101. Rather, the blue blood 175 (labeled with a reference numeral only in FIG. 1) will simply flow from these veins 140, 141 into the right atrium 101.

As described above, there are four (4) pulmonary veins 146, two veins for each lung 110. These pulmonary veins 146 return oxygenated red blood 165 (labeled with a reference numeral only in FIG. 1) from the lungs 110 to the left atrium 102. There are also two (2) pulmonary arteries 148a, 148b, one artery for each lung 110. The left pulmonary artery 148a carries blue blood 175 from the right ventricle 103 to the left lung while the right pulmonary artery 148b carries blue blood 175 from the right ventricle 103 to the right lung. In order to exit the heart 100 and enter the pulmonary arteries 148a, 148b, the blood 12a must pass through the pulmonary valve 138.

As noted above, one problem that may occur with the heart 100 is that of a "leaky valve" (e.g., a situation where one or more of the valves do not work properly). When working properly, the heart's naturally-occurring valves (e.g., the tricuspid valve 125, the mitral valve 120, the aortic valve 130 or the pulmonary valve 138) only allow blood 12a to flow in one direction (based upon the heart's pumping action). However, when one of these valves is "leaky," the valve does not "close" properly and allows blood 12a to "backflow" (i.e., flow in the opposite direction). For example, if the mitral valve 120 is leaky, blood 12a will be allowed to backflow from the left ventricle 105 to the left atrium 102. If the tricuspid valve 125 is leaky, blood 12a will backflow from the right ventricle 103 into the right atrium 101. If the aortic valve 130 is leaky, blood 12a will backflow from the aorta 132 into the left ventricle 105. If the pulmonary valve 138 is leaky, blood 12a may backflow from the pulmonary arteries 148a, 148b into the right ventricle 103.

If a patient has one or more leaky valves, it is possible to see this backflow of blood 12a in the patient's neck as the neck swells up and down due to the pressure caused by the back-flowing blood. More specifically, when the tricuspid valve 125 is not functioning properly, the blood 12a will pressurize the superior and inferior vena cavas 140, 141, which is revealed by a pulsing of the patient's veins in the neck. This causes back pressure and lack of proper circulation through the liver and kidneys, which leads to fluid build-up and low-functioning or non-functioning kidney and/or liver. Often this shutdown of the kidneys/liver will cause acidosis or toxicity in the blood 12a.

As described above, if the patient has at least one leaky valve, then the patient will likely need to undergo a valve-replacement surgery. In this surgery, one or more of the natural valves are either replaced by a mechanical one-way valve, or the leaky valve is repaired. Obviously, this surgery is very invasive. Moreover, if this valve-replacement surgery involves replacing the mitral valve 120 and/or the tricuspid valve 125, such a surgery involves cutting open the heart 100. Thus, this surgery is very invasive, very expensive, and can be very dangerous. As noted above, some patients who have an already weakened heart 100 would not survive the stress associated with a valve-replacement surgery. However, the present embodiments address these issues, as shown by FIG. 2.

Figure 2:
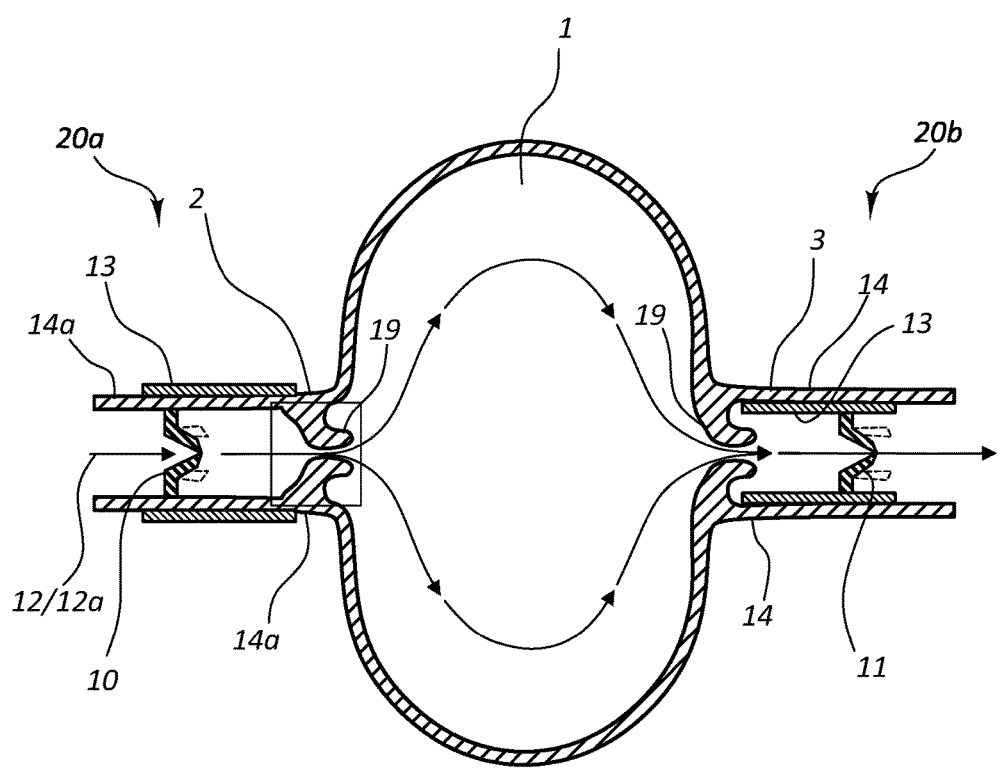
FIG. 2 is a schematic drawing of a vein, a heart, and an artery in which the present valves have been incorporated.

Specifically, FIG. 2 provides a simplified example of the heart together with a schematic view of the apparatus 20a-b. This apparatus 20a-b may be used in a patient, and more particularly, in a patient that has heart problems. In FIG. 2, the heart 1 is shown with a generic vein 2 (illustrated in FIG. 2) entering the heart 1 (such as the superior/inferior vena cava 140, 141 or the pulmonary veins 146, which are illustrated in FIG. 1B) and a generic artery 3 (illustrated in FIG. 2) exiting the heart 1 (such as the aorta or the pulmonary arteries 148a, 148b, which are illustrated in FIG. 1B). Blood 12a flows through the vein 2, into and out of the heart 1, and into and the through the artery 3, when the heart 1 pumps (beats). The direction of the blood flow is indicated by the arrow 12. (The vein 2 operates as the conduit for blood 12a into the heart 1 whereas the artery 3 operates as the conduit for blood 12a out of the heart 1.) Furthermore, FIG. 2 also shows a schematic representation of a naturally-occurring heart valve 19. This heart valve 19 may be leaking/damaged and thus will be referred to herein as a "damaged heart valve" 19. This damaged heart valve 19 is shown schematically at the entrance (inlet) and/or outlet of the heart 1. Those skilled in the art will appreciate where the exact location of the damaged heart valve 19 will be within the heart 1.

FIG. 2 illustrates a one-way prosthetic valve 10 placed outside of the heart 1. More specifically, the valve 10 is shown outside of the heart 1 (upstream) and within the vein 2. The valve 10 allows blood 12a to flow in its natural direction (i.e., in the direction of the arrow 12). Thus, when blood 12a is flowing, the blood 12a may flow into the heart 1, through the vein 2. However, the one-way function of the valve 10 is to prevent backflow of the blood 12a (e.g., flow away from the heart 1 into the vein 2). In other words, the one-way valve 10 ensures that blood 12a only flows in one direction and does not regurgitate, even if the native heart valve 19 leaks and allows regurgitation.

Blood 12a is a fluid and thus, it does not easily compress. Therefore, the one-way valve 10 does not need to be placed directly in the heart 1. Rather, as shown by FIG. 2, the valve 10 may be placed outside of the heart 1 and the beating of the heart 1 will still cause the valve 10 to close based upon the pumping. The valve 10 is placed outside of the heart 1 as a means of stopping backflow of blood 12a caused by a "leaky" valve 19. Even if the leaky valve 19 is actually inside the heart 1, as shown by the native heart valve 19 (e.g., the mitral valve 120 or the tricuspid valve 125, which are illustrated in FIG. 1B), the placement of the prosthetic valve 10 outside the heart 1 helps to solve the problems associated with backflow of blood 12a.

In the embodiment shown in FIG. 2, an additional prosthetic one-way valve 11 has been added. Specifically, this valve 11 is positioned within the artery 3. This valve 11 also operates to ensure that blood 12a does not backflow. In other words, this valve 11 may work with the valve 10, or by itself, to assist pumping efficiency. When the heart 1 relaxes or expands from its squeezing action, the one-way prosthetic valve 11 closes and the one-way prosthetic valve 10 opens, allowing blood 12a to enter the heart 1. When the heart 1 pumps or squeezes, the pressure operates to close the prosthetic valve 10, forcing blood 12a out through the artery 3, and the one-way prosthetic valve 11. Thus, by having these two valves 10, 11 work in concert, the backflow of the blood 12a may be eliminated or reduced. In some embodiments, the valves 10, 11 may be controlled via electrical stimuli or other controls (such as from an electrical micro-controller/controller), thereby ensuring that they properly work in concert.

While FIG. 2 shows the use of valve 10 and valve 11, it should be noted that embodiments may be constructed in which only the valve 10 in the vein is used. In other embodiments, only the valve 11 in the artery will be used. In further embodiments, multiple valves 10 may be used in the vein(s) without any valves 11 being used in the artery(ies). In other embodiments, multiple valves 11 may be used in the artery(ies) without any valves 10 being used in the vein(s). In further embodiments, one or more valves 10 in the vein(s) may be used with one or more valves 11 in the artery(ies). Further embodiments may be designed in which the one or more valves 10, 11 work in conjunction with other valves (including the naturally-occurring heart valves).

The sleeve illustrated in FIG. 2 is a cylindrical shaped device and may be placed outside the wall(s) 14a of the vein 2. This sleeve 13 may also be a stent, spring-type device, wrapped mesh, or string or other feature. The purpose of this sleeve 13 is to provide additional support/structural integrity to the vein 2. Accordingly, any structure that is capable of performing this strengthening function may be used as the sleeve 13. Because of added pressure and stress to the vein 2, possibly caused by the one-way valve 10, the sleeve 13 strengthens and supports the walls of the vein 2. If the sleeve 13 was not present, the vein 2 may otherwise expand, burst or be damaged by the placement/operation of the valve 10. However, because the sleeve 13 prevents expansion of the vein 2, it maintains the efficiency of the heart 1 during the pumping/relaxation of the heart 1.

Likewise, the artery 3 also may have a sleeve 13 used in conjunction with the valve 11, thereby strengthening the wall(s) 14 of the artery 3. However, the sleeve 13 that is placed around the artery 3 is placed within the walls of the artery 3 (e.g., inside the artery 3). Those skilled in the art will appreciate that the sleeve 13 may be added either outside of the walls of the vein 2 or artery 3 or inside of the walls of the vein 2 or artery 3, depending upon the particular embodiment and/or the condition of the patient and/or the ease of access to the vein 2 or artery 3. In fact, the position of the sleeve 13 (i.e., whether the sleeve 13 is on the outside or the inside of the vein 2 or artery 3) may determine which exact type of material is used for the sleeve 13 (such as whether the sleeve 13 is a string, a tube, wrapped mesh, etc.). It should be noted that the use of the sleeve 13 may be particularly advantageous when associated with the valve 11 that is downstream from the heart 1. In the case of a valve 11 being placed after the exit of a heart 1, vacuum conditions may be experienced as part of the heart pumping action. By placing the sleeve 13 (or stent, etc.) inside of the artery 3, this sleeve 13 may keep the artery 3 open under the vacuum phase of pumping, which vacuum will likely be present if an exit valve is placed downstream of the heart 1.

Figure 3:
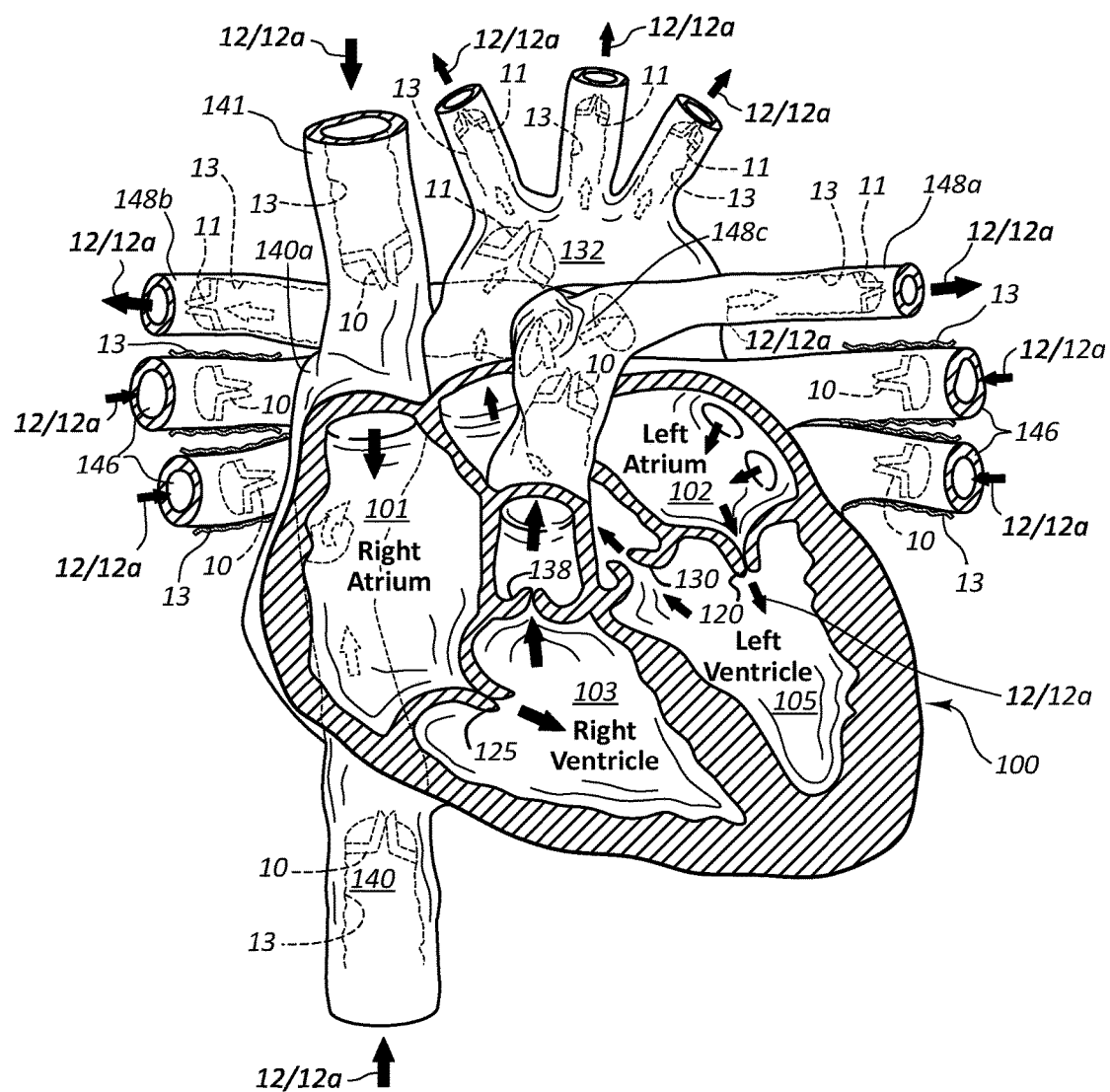
FIG. 3 is an isometric drawing similar to FIG. 2 in which the present valves have been incorporated therein.

It will be readily apparent that the embodiments outlined in the simplified drawing of FIG. 2 can readily be adapted to the actual human heart 100 shown in FIG. 3. More specifically, FIG. 3 shows a drawing of a heart 100, with arteries and veins, that is similar to that which is shown in FIG. 1B; however, in the embodiment of FIG. 3, various valves, according to the present embodiments, have been added to the various veins/arteries. Once again, in FIG. 3, the direction of blood flow is represented by arrows labeled with reference numeral 12, while the blood itself is represented by reference numeral 12a.

More specifically, the veins shown in FIG. 3, which are the superior vena cava 140 and inferior vena cava 141 along with the four (4) pulmonary veins 146, each have had a one-way valve 10 added thereto. (The superior vena cava 140 and inferior vena cava 141 join in a "T" junction 140a.) However, those skilled in the art will realize that not all of these veins 140, 141, 146 need to have the valve 10. One or more of these veins 140, 141, 146 (but not all) may have the valves 10. A valve 10 may also be positioned within the T junction 140a. However, other embodiments may be constructed in which all of these veins (i.e., the veins carrying blood 12a to the heart 100) include at least one valve 10. It should also be noted that additional embodiments may be constructed in which more than one valve 10 is placed within the same vein. For example, embodiments may be designed in which multiple valves 10 are placed within the pulmonary veins 146 and/or within the superior or inferior vena cava 140, 141, etc. Those skilled in the art will appreciate the various permutations/combinations that may be implemented regarding the use of valve(s) within the veins.

FIG. 3 further illustrates that the valves 10 may be used with the optional sleeve 13. In some embodiments, the sleeve 13 may be placed within the walls of the vein, whereas other embodiments may be designed in which the sleeve 13 is positioned outside of the walls of the vein. Additional embodiments are designed in which some of the sleeves 13 are positioned inside of the walls and some of the sleeves 13 are positioned outside of the walls. Furthermore, those skilled in the art will appreciate that multiple sleeves 13 could be used on a single vein, as desired. Again, there are a variety of permutations/combinations that may be implemented using the sleeves 13.

As shown in FIG. 3, the valves 11 may also be used with the arteries, such as the pulmonary arteries 148a, 148b and/or the aorta 132. (A valve 11 may also be placed within the junction 148c of the left and right pulmonary arteries 148a, 148b.) More specifically, one or more of these arteries may receive a valve 11 (or more than one valve 11). Furthermore, a sleeve 13, or more than one sleeve 13, may be used with these arteries, regardless of whether the sleeve 13 is inside or outside of the wall of the artery. In some embodiments, the valves 11 will be added to all of the arteries that take blood 12a from the heart 100, whereas other embodiments may only have some of the arteries that take blood 12a from the heart 100 receive the valve 11. Again, there are a variety of permutations/combinations that may be implemented using the sleeves 13 and/or the valves 11 that are all within the scope of the present disclosure.

FIG. 3 also illustrates that embodiments may be constructed in which the valves 10 placed in the veins are used in conjunction with the valves 11 in the arteries. More specifically, the one or more valves 10 used with the veins may be referred to as first one-way valve(s) 10 (or a first set of one-way valves 10) and the one or more valve 11 used with the arteries may be referred to as second one way valve(s) 11. Embodimentsmay be constructed in which one or more of the first and second one-way valves 10, 11 are both used on the same patient.

In some embodiments, multiple (i.e., two or more) valves 10, 11 may be used in the same vein/artery. In other words, these multiple valves 10, 11 may be placed in series within the vein/artery. Obviously, these valves 10, 11 will be spaced apart, such as somewhere between 1-10 mm apart. (Of course, other distances may also be used.) The use of such valves 10, 11, in series, may be beneficial depending upon the severity of the patient's CHF condition.

Additional embodiments may be constructed in which the valve 10 and/or the valve 11 are positioned 1 to 5 mm away from the heart 100 (e.g., either upstream or downstream of the heart 100.) However, these distances are not limiting. In other embodiments, the one-way valves 10, 11 may be positioned 6-10 mm away from the heart, 11-20 mm away from the heart 100, etc. Distances greater than 20 mm may also be used. In other embodiments, the distance between the first valve 10, 11 (in a series of valves 10, 11) and the heart 100 is less than or equal to 10 inches. In further embodiments where multiple valves 10, 11 are used in series within the same artery/vein, these valves 10, 11 may be positioned about 5 mm apart, about 10 mm apart, etc., as desired.

One of the significant advantages of the present embodiments is that the valves 10, 11 that are used can be relatively simple. Any device that is capable of operating as a "one-way" valve (i.e., allowing fluid flow in only one direction and preventing backflow) may be used with the present embodiments. For example, U.S. Pat. Nos. 6,719,787 and 6,736,846 describe various types of heart valves that have been used. All of these valves, along with other types of devices, may be used as the valves 10, 11 in the present embodiments. Mechanical and/or naturally-occurring valves may also be used as the valves 10, 11 of the present embodiments.

In some embodiments, there may be significant advantages to the present use of valves 10, 11 outside of the heart. For example, the present embodiments may be implemented/implanted into a patient, wherein the patient's natural valves (which may or may not be leaky) are untouched. Thus, if a patient has a leaky mitral or tricuspid valve (e.g., valves within the heart), the present embodiments can be implemented into the patient outside of the patient's heart. Thus, the patient can rectify these leaky valves without having to have his/her heart 100 cut open. Rather, the patient's existing valves may be untouched.

Furthermore, a huge economical advantage of the present embodiments is that many people who otherwise could not be helped by a doctor, unless they actually received a heart transplant, could be helped by the present embodiments. In other words, some patients that currently have such late stages of CHF such that the only treatment for them is a heart transplant. The present embodiments could be used on these patients and provide them with benefits, without requiring these patients to actually receive a heart transplant. Furthermore, because the surgery of implanting the present embodiments may be endoscopic, these patients with late-stage CHF could actually survive the surgery implanting the present embodiments.

Additionally, not only people in congestive heart failure could benefit from the present embodiments but also people who simply have leaky heart valves may also benefit. The present embodiments would not hurt or damage their existing valves and would likely prevent their existing valves from becoming worse due to an enlargement of their heart. Furthermore, for these patients, even if the implanted valves 10, 11 fail, the patient can still live to get another one of the present valves 10, 11, because they still have their original (naturally-occurring) working heart valves in their bodies.

As described above, when the tricuspid valve is not functioning properly, the blood will pressurize the superior and inferior vena cavas, which is manifest by a pulsing in the neck of the patient. This causes back pressure and lack of proper circulation through the liver and kidneys, which leads to fluid build-up and low-functioning or non-functioning kidneys/liver. Often this shut down of the kidneys/liver will cause acidosis or toxicity in the blood. However, a simple valve 10 placed in the inferior vena cava would likely prevent this backflow and would also prevent pressure from being exerted on the liver and kidneys. Thus, the present embodiments could address the issues of backflow pressure on the liver/kidneys. In some embodiments, two or more valves may be used in this situation, one closer (upstream) to the heart 100 and one downstream of the heart 100. As indicated above, the valve 10, 11 of the present invention may be in a fluid tight engagement with the associated vein or artery, when surgically implanted within a patient, in order to prevent backflow through the valve 10, 11 when the valve 10, 11 is in a closed state.

The present embodiments also involve a process in addition to an apparatus. More specifically, the present embodiments include a process for inserting one or more valves 10, 11 into a patient. The valves 10, 11 may be inserted into one or more of the patient's veins, one or more of the patient's arteries, and/or both veins/arteries. At the same time, the valve(s) 10, 11 are not inserted into the heart 100, but are inserted either upstream or downstream of the heart 100. Because the valve(s) 10, 11 are not placed into the heart 100, the patient's heart 100 does not need to be "cut open" during this surgery. In fact, the patient's naturally-occurring valves (such as the tricuspid valve, mitral valve, pulmonic valve and aortic valve) are left untouched during the surgery. Thus, if the present mechanical valves 10, 11 fail, the patient's original, naturally-occurring valves are still in place and can function. To further support the valves 10, 11 that are placed in the veins/arteries, one or more sleeves/stents may be added thereto. It should also be noted that the insertion of the valve(s) 10, 11 described herein may be performed endoscopically, thereby decreasing the patient's recovery time and limiting the amount of incisions into the patient's body. Of course, in other embodiments, the valves 10, 11 may be placed using normal surgical procedures that may involve cutting the patient open. As shown in FIGS. 2-3 and as indicated above, in various embodiments, when in place within the patient following the one or more surgical procedures, all portions of the valve 10, 11 and any components 13 connected to the valve 10, 11 may be disposed completely outside of any chamber 101, 102, 103, 105 of the heart 100. As further shown in FIGS. 2-3, in various embodiments, there is no intermediary component securing, directly or indirectly, one of the valves 10, 11 to another one of the valves 10, 11.

All the journal articles, patent applications and patents listed herein are expressly incorporated herein by reference.

What is claimed is:

1. An apparatus comprising:
a one-way valve configured to be placed inside a vein that supplies blood to the heart of a patient through one or more surgical procedures, the valve configured to remain in place within the patient following the one or more surgical procedures, the valve configured to be placed upstream of the heart such that, when in place within the patient following the one or more surgical procedures, all portions of the valve and any components connected to the valve are disposed completely outside of any chamber of the heart, wherein the valve is configured to increase pumping efficiency of the heart,
the valve being configured to be placed at a distance of 10 inches or less away from the heart through the one or more surgical procedures; and
a sleeve configured to abut a portion of the vein between the valve and the heart through the one or more surgical procedures such that, when in place within the patient following the one or more surgical procedures, the sleeve mitigates expansion of the vein between the valve and the heart.

2. The apparatus of claim 1, wherein the one-way valve is configured to be placed within the superior vena cava and a second one-way valve is configured to be placed within the inferior vena cava through the one or more surgical procedures.

3. The apparatus of claim 1, wherein the one-way valve is configured to be placed upstream of the T junction where the superior vena cava meets the inferior vena cava through the one or more surgical procedures.

4. The apparatus of claim 1, wherein the valve is configured to be placed at least 1 millimeter away from the heart through the one or more surgical procedures.

5. The apparatus of claim 4, wherein the valve is configured to be placed within 20 millimeters of the heart through the one or more surgical procedures.

6. The apparatus of claim 4, wherein the sleeve is further positioned around a portion of the vein in which the one-way valve is situated.

7. The apparatus of claim 1, wherein the valve is configured to be placed in one or more of the pulmonary veins of the patient through the one or more surgical procedures.

8. The apparatus of claim 1, wherein no natural valve of the heart is removed when the valve is placed within the vein through the one or more surgical procedures.

9. An apparatus comprising:
one or more first one-way valves configured to be placed inside one or more veins that supply blood to the heart of a patient through one or more surgical procedures, the one or more first one-way valves configured to remain in place within the patient following the one or more surgical procedures, the one or more first one-way valves configured to be placed upstream of the heart such that, when in place within the patient following the one or more surgical procedures, each of the one or more first one-way valves are disposed at a distance of 10 inches or less away from the heart and all portions of the one or more first one-way valves and any components connected to the one or more first one-way valves are disposed completely outside of any chamber of the heart;
one or more second one-way valves configured to be situated inside one or more arteries that take blood from the heart through the one or more surgical procedures, the one or more second one-way valves configured to remain in place within the patient following the one or more surgical procedures, the one or more second one-way valves configured to be placed downstream of the heart such that, when in place within the patient following the one or more surgical procedures, each of the one or more second one-way valves are disposed at a distance of 10 inches or less away from the heart and all portions of the one or more second one-way valves and any components connected to the one or more second one-way valves are disposed completely outside of any chamber of the heart,
wherein the one or more first one-way valves and the one or more second one-way valves, when in place within the patient following the one or more surgical procedures, are devoid of any intermediary component that directly or indirectly secures any of the one or more first one-way valves to any of the one or more second one-way valves or to any other of the one or more first one-way valves.

10. The apparatus of claim 9, further comprising multiple first one-way valves, wherein each of the first one-way valves is configured to be placed within a different vein when in place within the patient through the one or more surgical procedures, and further comprising multiple second one-way valves, wherein each of the second one-way valves is configured to be placed within a different artery when in place within the patient through the one or more surgical procedures.

11. The apparatus of claim 1, wherein the one-way valve is in fluid tight engagement with an interior surface of the vein when in place within the vein following the one or more surgical procedures.

* * * * *